United States Patent [19]
Morris

[11] Patent Number: 5,936,536
[45] Date of Patent: Aug. 10, 1999

[54] ELECTRICAL INSULATION TESTING DEVICE AND METHOD FOR ELECTROSURGICAL INSTRUMENTS

[75] Inventor: James R. Morris, Sedalia, Colo.

[73] Assignee: MediCor Corporation, Wheeling, Ill.

[21] Appl. No.: 08/838,319

[22] Filed: Apr. 8, 1997

[51] Int. Cl.⁶ .................................................. G08B 21/00
[52] U.S. Cl. .................... 340/647; 340/664; 340/693.5; 361/42; 606/35; 606/46
[58] Field of Search .................... 340/647, 664, 340/693.5; 361/42; 606/35, 38, 42, 46, 48

[56] References Cited

U.S. PATENT DOCUMENTS

| | | |
|---|---|---|
| 4,231,371 | 11/1980 | Newton ....................................... 361/42 |
| 5,312,401 | 5/1994 | Newton et al. ............................ 606/46 |
| 5,688,269 | 11/1997 | Newton et al. ............................ 606/46 |
| 5,769,841 | 6/1998 | Odell et al. ................................ 606/52 |

*Primary Examiner*—Daniel J. Wu
*Attorney, Agent, or Firm*—Olson & Hierl, Ltd.

[57] ABSTRACT

A device suitable for testing the integrity of insulation coating an electrosurgical instrument is described. The device includes a test sleeve and a fault detection unit. The test sleeve is generally tubular and defines an open bore with a resilient conductive lining mounted therein. The fault detection unit is coupled to the conductive lining such that establishment of an erroneous current path between the conductive lining and an electrosurgical device is detected.

31 Claims, 5 Drawing Sheets

ELECTRICAL INSULATION TESTING DEVICE AND METHOD FOR ELECTROSURGICAL INSTRUMENTS

FIELD OF THE INVENTION

The present invention relates to test devices and methods, and in particular to an electrosurgical test device and method for verifying whether insulation on the outer surface of an electrosurgical instrument is adequate to prevent the formation of undesirable current paths.

BACKGROUND OF THE INVENTION

Electrosurgical systems which use high frequency electrical current for cutting and/or coagulation of human tissue are well known in the art. Normally, the electrical current is applied to preselected tissue by using an electrosurgical instrument such as a unipolar electrode.

The typical unipolar electrode consists of a surgical grade stainless steel shaft or similar substrate that is substantially coated on its outer surface with an insulative (i.e., electrically nonconductive) coating. The tip of the substrate is exposed and defines the working surface of the instrument which may be configured in the shape of a hook.

During surgery, a conventional electrosurgical generator is used to energize the electrode substrate. The tip of the electrode is brought into contact with preselected tissue of a patient which results in a current path being provided between the electrode and the patient.

The current from the electrode develops a high temperature region about the electrode's tip which destroys tissue. The current is returned to the electrosurgical generator by means of a return electrode attached to the patient.

The widespread application and growth of electrosurgery has given rise to a large variety of specialized electrodes. For example, many surgical specialties (e.g., Neurosurgery, Cardiovascular surgery, General surgery, etc.) currently utilize some form of electrosurgery and hence electrosurgical instrumentation. As such, many different types of electrodes and electrode tip configurations are available such as a knife tip, cone tip, button tip, spatula tip, sling tip, scissor tip, forcep tip, and the like.

Although electrosurgery provides numerous advantages, there are several significant risks associated with electrosurgery. Numerous incidents of inadvertent electrical shocks and burns to the patient, and even death, have been reported. In a great number of these cases, the injury was due to the electrical insulation on the electrode shaft becoming worn, breaking down, or developing small pin holes. Thus, current is allowed to inadvertently pass from the electrode onto tissue or organs not intended to be altered.

Many materials used in providing electrode insulation typically lack durability. Illustrative insulation coatings consist of fluorocarbons such as poly (tetrafluoro-ethylene), a poly (vinyl chloride) (PVC), or a heat-shrinkable plastic. While these materials have well-documented electrical insulative characteristics, they are not optimally suitable for use with electrosurgical instrumentation. The major weakness of these coatings is their inadequate abrasion resistance (i.e., the coating rubs off easily leaving bare metal exposed), and decomposition of the coating at relatively high temperatures used in sterilization and in the electrosurgical process itself.

The lack in being able to detect whether an electrode that has been used in one or more surgical procedures still retains a reliable insulation coating necessitates the continued replacement of the insulation or the entire electrode. However, the risk of inadequate insulation on a new or refurbished electrode is still present because the insulation coating may have been defectively applied, damaged during shipping, or prematurely became worn-out.

Correspondingly, the present invention pertains to a device and method which detects defective electrosurgical insulation by providing for testing of the insulation before performing a surgical procedure.

SUMMARY OF THE INVENTION

The present invention provides an electrosurgical test device and method for inspecting the quality of insulation that coats an electrosurgical instrument.

The device embodying the present invention is especially suitable for minimizing the likelihood of using an electrosurgical instrument having defective insulation on its outer surface. As such, the test device substantially reduces the risk of stray current flowing through a patient's body during an electrosurgical procedure. Furthermore, the test device provides for easy cleaning by disconnecting and disposing of contaminated test device elements.

The electrosurgical test device embodying the present invention includes a test sleeve assembly and a fault detection unit. The test sleeve assembly is generally tubular and defines an open bore. Mounted to the sleeve within the bore is a resilient conductive lining. The fault detection unit is detachably coupled to the conductive lining. The fault detection unit provides for detection of an erroneous current path between the conductive lining and an electrosurgical instrument.

BRIEF DESCRIPTION OF THE DRAWINGS

In the accompanying drawings that form part of the specification, and in which like numerals are employed to designate like parts throughout the same.

DESCRIPTION OF THE PREFERRED EMBODIMENTS

The present invention provides an electrosurgical test device for verifying the integrity of insulation coating an electrosurgical instrument. The test device includes a disposable test sleeve and a fault detection unit. The test sleeve is generally tubular in shape and defines an open bore with a resilient conductive lining mounted therein. The fault detection unit is coupled to the conductive lining such that erroneous passage of current between the conductive medium and an electrosurgical lining is detected.

Figure 1:
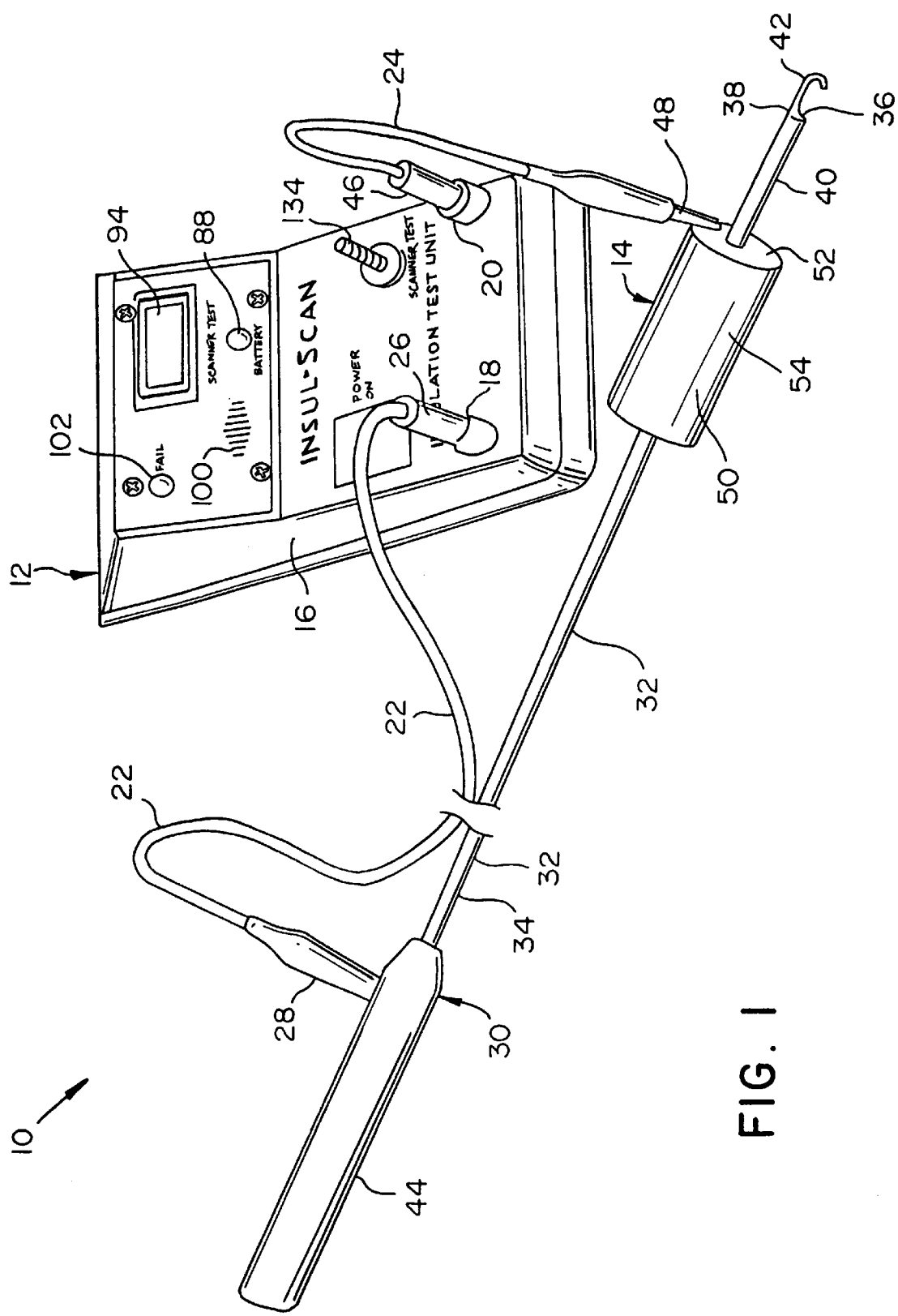
FIG. 1 is a top perspective view of an electrosurgical test device in accordance with the present invention and having a fault detection unit operably connected to a test sleeve assembly that extends around an electrosurgical instrument.

Referring to the drawings, and particularly to FIG. 1, an electrosurgical test device in accordance with the present invention is depicted. The test device 10 includes a fault detection unit 12 and a test sleeve assembly 14.

The fault detection unit 12 has an outer nonconductive plastic housing 16 with a supply voltage output terminal 18 and a return terminal 20. Connected to terminals 18 and 20 are a supply lead 22 and a return lead 24, respectively.

The supply lead 22 has a plug 26 on one end and a receptacle 28 on the other end. The plug 26 is coupled to the detection unit supply terminal 18. Further, the receptacle 28 is detachably connected to an electrosurgical instrument 30 for providing a conductive current path between the fault detection unit 12 and the electrosurgical instrument.

The electrosurgical instrument 30 includes a unipolar electrode having an elongated shaft 32 with a proximal end 34 and a distal end 36. The electrode shaft 32 consists of a conductive substrate 38, made from material such as stainless steel, with an outer coating of insulation material 40.

Figure 3:
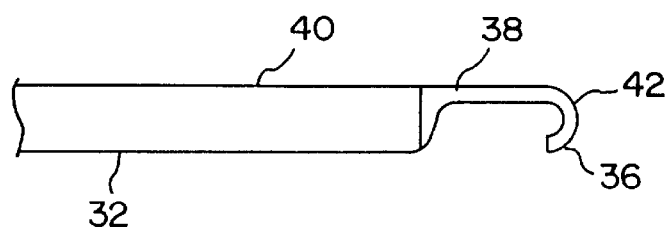
FIG. 3 is an enlarged side view of the distal end of the electrosurgical instrument shown in FIG. 1.

The coating of insulation material 40 extends on the outer surface of the shaft 32 from the proximate end 34 to a region about the distal end 36. As shown in FIGS. 1 and 3, the distal end 36 of the electrode 30 is not coated with insulation material such that the conductive substrate 38 is exposed. Further, the shaft distal end 36 may take the shape of, for example, a conductive hook tip 42 which is integral with the substrate 38.

Attached to the proximal end 34 of the electrode shaft 32 is an insulated handle 44 that allows for manually positioning the electrode 30. The handle 44 also provides a plug (not shown) for conductively connecting the electrode 30 to a voltage supply. Thus, with the receptacle 28 of the supply lead 22 connected to the plug of the electrode 30, a conductive path is provided from the detection unit 12, through the electrode shaft 32, to the exposed hook tip 42 of the electrode.

Although electrode 30 is shown and described above as a unipolar electrode with a hook tip, it should be understood that other types of electrosurgical instruments can be tested with the present invention. For instance, electrosurgical forceps, bipolar electrodes, and other types of electrosurgical instruments may be so tested, if desired.

As shown in FIG. 1, return lead 24 is coupled to the fault detection unit 12 and has a plug 46 at one end and an alligator clip type connector 48 on the other end. The plug 46 is coupled to the detection unit return terminal 20. Further, connector 48 is detachably coupled to the test sleeve assembly 14 for providing a current return path between the test sleeve and the fault detection unit 12.

Figure 2:
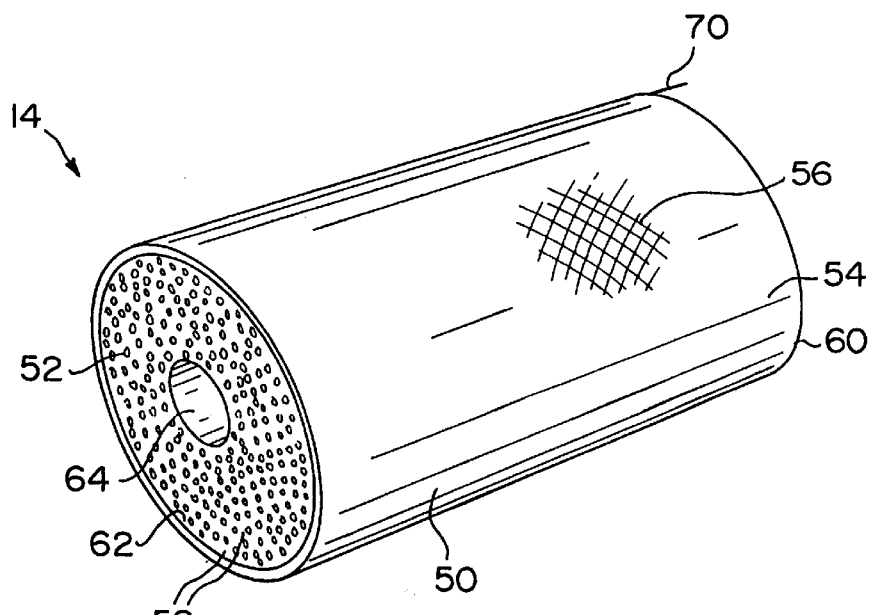
FIG. 2 is an enlarged top perspective view of the test sleeve assembly of FIG. 1 with the electrosurqical instrument removed.
Figure 4:
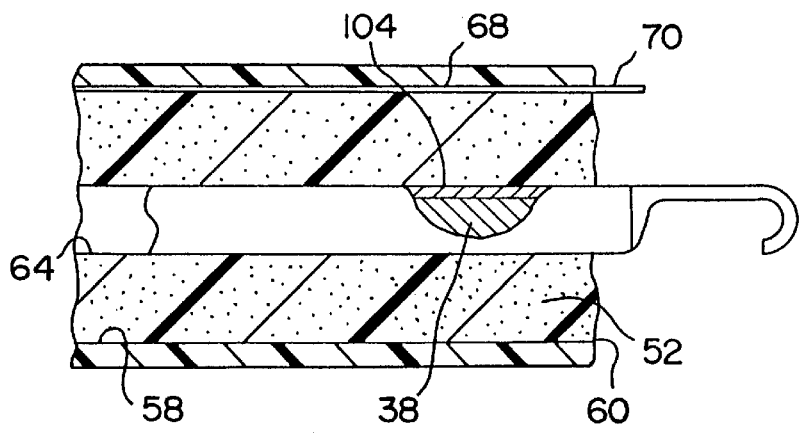
FIG. 4 is an enlarged cross-sectional side view of the test sleeve assembly of FIG. 1 with the electrosurgical instrument extending through an open passageway in the test sleeve and having a defective insulation coating.

Turning to FIGS. 2 and 4, the test sleeve assembly 14 includes a cylindrical outer sheath 50 surrounding a conductive lining 52. The sheath 50 preferably consists of an electrically insulative rigid material such as a nonconductive plastic with a longitudinal length of about 1.8 centimeters (cm). The outer surface 54 of the sheath 50 is knurled 56 to aid in securely manually gripping onto the test sleeve assembly 14 by hand.

The sheath 50 defines a cylindrical open bore 58 with a first open end 60 and an opposite second open end 62. The conductive lining 52 is contained within the bore 58 and extends proximate to the open ends 60, 62 of the sheath 50. The conductive lining 52 defines a tubular expandable open passageway 64 generally in longitudinal axial alignment with the sheath 50. The lining 52 is secured to the inner surface 66 of the sheath 50 by epoxy or similar means.

The lining 52 preferably consists of a conductive resilient material such as, for example, a conductive foam used in providing electrostatic discharge (ESD) protection to semiconductor integrated circuits. Foams of this type include, but are not limited to, conductive crosslinked polyethylene or copolymer foams. As an alternative, the lining 52 may utilize another type of resilient conductive media such as metal bristles, conductive gel, wet leather, or any other suitable lining material.

It is desirable for the tubular expandable open passageway 64 formed by the conductive lining 52 to have an initial inner diameter that is smaller than the outer diameter of the electrode shaft 32. In such an embodiment, the conductive lining 52 expands to allow the electrode shaft 32 to slide through the passageway 64. Further, the lining 52 resiliently presses against the outer surface of the shaft 32 such that the lining may extend into openings or fissures in the electrode insulative coating 40. Thus, the lining 52 preferably comes into direct electrical contact with the electrode conductive substrate 38 in those areas where insulation material 40 is lacking.

Extending between the sheath 50 and the lining 52 is an elongated post 68 consisting preferably of a conductive metal or metal alloy. The post 68 is generally in longitudinal alignment with the sheath 50 and an end 70 of the post protruding a fixed distance from the sheath first end 60.

The post 68 is secured to the inner surface 66 of the sheath 50 by an adhesive or the like. Further, the post 68 is in electrically conductive contact with the lining 52 mounted in the sheath 50. Thus, with the clip 48 of the return lead 24 connected to the end 70 of post 68 as shown in FIG. 1, a conductive path is provided from the conductive lining 52, through the post 68 and the return lead 24, to the return terminal 20 of the fault detection unit 12.

Figure 5:
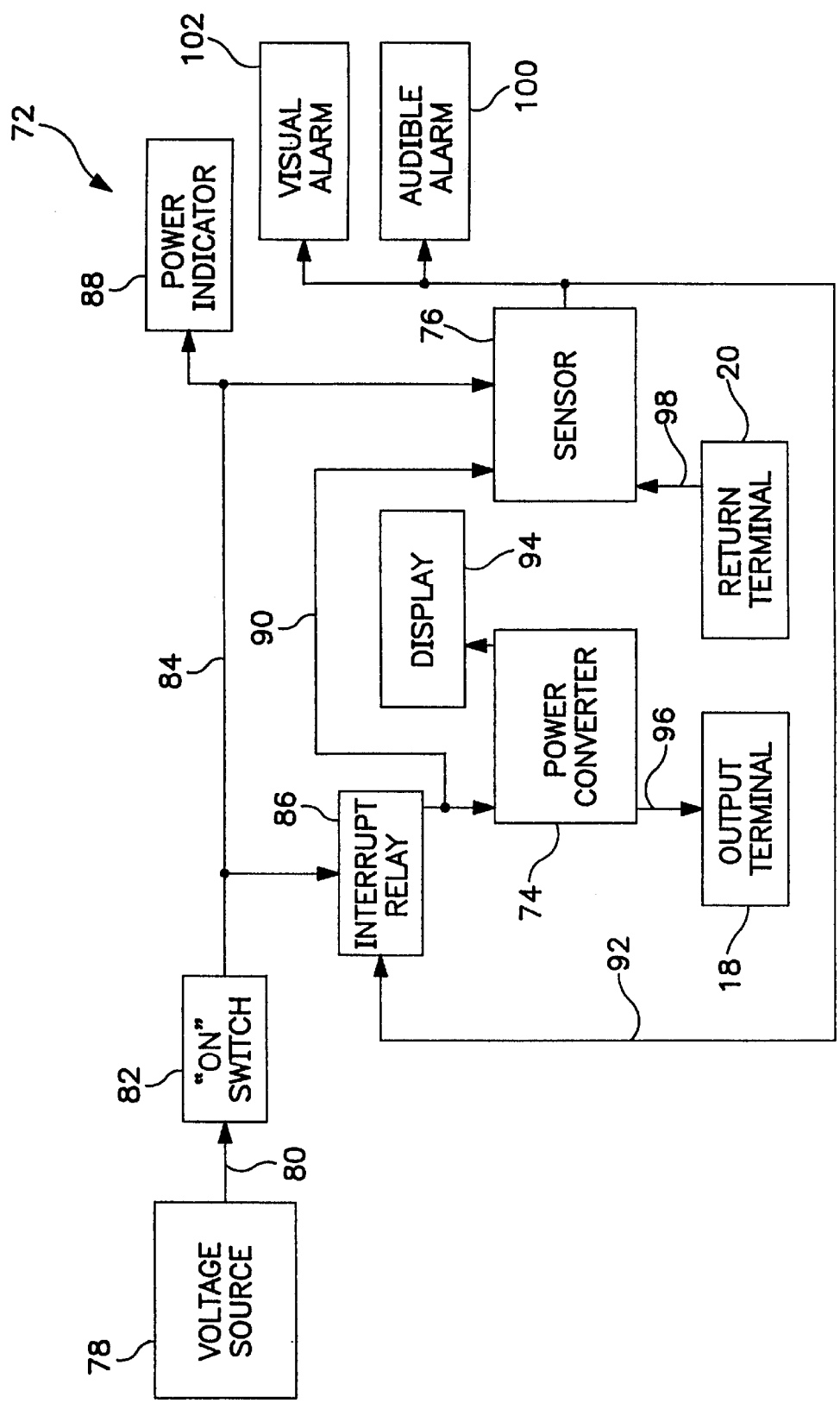
FIG. 5 is an electrical circuit diagram in block form of the fault detection unit shown in FIG. 1.

FIG. 5 shows an electrical circuit diagram, in block form, of a fault detection circuitry provided by the detection unit 12. Within FIG. 5, a single block may indicate several individual components and/or circuits which collectively perform a single function. Likewise, a single line may represent several individual signal or energy transmission paths for performing a particular operation.

The fault detection circuitry 72 includes both a power converter 74 and a sensor 76. Power for operating the detection circuitry 72 is provided by a voltage source 78 that preferably furnishes a voltage potential 80 of approximately nine (9) volts DC.

The voltage potential 80 is received by an "on" switch 82 for simultaneously switching power either off or on to sensor 76, a power interrupt relay 86, and a power indicator 88. When enabled (i.e., toggled to an "on" position), the switch 82 couples voltage potential 80 to relay 86, sensor 76, and indicator 88, via lead 84. Likewise, when the switch 82 is disabled (i.e., toggled to an "off" position), the voltage potential 80 is disconnected from lead 84 which turns the fault detection circuitry 70 off.

Power indicator 88 provides for visually indicating if the "on" switch 82 has been selected to transfer power to the fault detection circuitry 72, and in particular, the interrupt relay 86 and the sensor 76. Preferably, power indicator 88 is coupled to lead 84 and includes a Light Emitting Diode (LED) which illuminates only when power is being provided, via switch 82, from the voltage source 78 to the indicator, relay 86, and sensor 76.

The interrupt relay 86 conveys an enable signal 90 that is received by the power converter 74 and the sensor 76. Preferably, the interrupt relay 86 is manually selectable (i.e., toggled) to activate enable signal 90 such that lead 84 and enable signal 90 are coupled together. Thus, by connecting lead 84 to the enable signal, power is supplied to the converter 74 if switch 82 is toggled "on."

The interrupt relay 86 also receives a fault detection signal 92 generated by sensor 76. Preferably, the fault detection signal 92 has two states: (1) one state indicates detection of a fault in the electrosurgical instrument insulation and (2) the other state signifies that no fault has been detected.

If the state of the detection signal 92 indicates detection of a fault, the interrupt relay 86 responds by removing power from the converter 74. As indicated above, power is removed by disconnecting the enable signal 90 from lead 84.

In addition to being coupled to the interrupt relay 86, the power converter 74 is attached to a display 94 and the output terminal 18. The power converter 74 boosts the voltage potential 80 from the voltage source 78 to provide output terminal 18 with a high voltage potential 96 that is greater than the input voltage potential 80. Desirably, the high voltage output 96 is between 1,500 and 2,000 volts direct-current and, preferably, is about 2 kilovolts direct-current.

The display 94 attached to the power converter 74 provides a visual indication of the magnitude of the high voltage potential 96 provided by the power converter. The display 94 is of conventional construction and may include an LED display, liquid crystal display, or the like.

As stated above, sensor 76 is attached to the interrupt relay 86 and the "on" switch 82. Further, the sensor 76 is coupled to the return terminal 20. The sensor 76 is responsive to receipt of a return current 98 from the return terminal 20. Reception of the return current 98 indicates the presence of a flaw in the insulation 40 of the electrode shaft 32. As explained in detail below, the return current 98 is provided by the power converter 74.

Until sensor 76 receives return current 98, the sensor maintains the fault detection signal 92 in a state indicating that no fault in the electrode insulation 40 has been detected. However, upon receiving return current 98, sensor 76 responses by changing the state of the fault detection signal 92 to indicate the presence of the fault.

Indication of a fault by sensor 76, via detection signal 92, results in the interrupt relay 86 providing feedback to the sensor for latching the state of the detection signal. Latching the detection signal 92 results in the presence of a fault continuously being indicated by the sensor 76 regardless of whether the return current 98 is still being received.

The fault detection signal 92 also is received by audible alarm 100 and visual alarm 102. Indication by the fault detection signal 92 of a fault in the electrode insulation 40 activates the audible alarm 100 and the visual alarm 102. When activated, the audible alarm 100 preferably produces a high pitch to indicate detection of the fault. Likewise, the visual alarm 102 preferably includes an LED that illuminates when signal 92 indicates the presence of a fault.

In FIGS. 1–5, the electrosurgical test device 10 is initially configured to test electrode 30 by inserting the electrode hook tip 42 into the test sleeve passageway 64. The electrode 30 is then partially pushed through the passageway 64 until the insulation 40 on the electrode shaft 32 separates the test sleeve lining 52 from the conductive portion 38 of the electrode.

Next, power to the fault detection circuitry 72 is provided by toggling switch 82 to the "on" position such that the voltage potential 80 from the voltage source 78 is asserted onto supply lead 84. Further, if required, interrupt relay 86 is manually positioned to provide power, via leads 84 and 90, to the power converter 74.

Upon receiving power, the power converter 74 generates the high voltage potential 96 that is received by the output terminal 18. The high voltage potential 96 is conveyed from the output terminal 18, through the supply lead 22, to the conductive substrate 38 of the elongated electrode shaft 32. The magnitude of the voltage potential 96 provided by the power converter 74 is presented by display 94.

The electrode shaft 32 is slid through the test sleeve passageway 64 such that, preferably, the entire coating of electrode insulation 40 is brought into contact with the sleeve lining 52. If, as shown in FIG. 4, a defect 104 is present in the insulation material 40 that exposes the conductive substrate 38 of the electrode 30, then a current path will be present between the output terminal 18 and return terminal of the fault detection unit 12.

The current path between the terminals 18, 20 preferably is caused by the lining 52 coming into direct physical contact with the electrode substrate 38. However, even if the substrate 38 and lining 52 fail to come into contact with each other, it is desired that the high voltage 96 provided by the power converter 74 be sufficient enough to cause the current to pass between the substrate and the lining 52 due to a sparkover, or the like, which passes through the defect 104.

The current flowing from the electrode substrate 38 to the conductive lining 52 is received by the fault detection unit sensor 76. The current path from the lining 52 to the sensor 76 extends through post 68, return lead 24, and return terminal 20.

Upon receipt of the return current 98, the sensor 76 changes the state of the fault detection signal 92 to indicate the presence of the fault in the electrode insulation 40. As such, both the audible alarm 100 and the visual alarm 102 are activated.

Further, the fault signal 92 trips the interrupt relay 86 for commanding the sensor 76 to latch the fault signal and disable the high voltage output 96 of the power converter 74. The removal of voltage potential to the power converter 74 by the interrupt relay results in the power converter ceasing to provide the high voltage potential 97 to the output terminal 16 and thus the electrode. Further, the latching of the fault detection signal 92 results in the visual alarm 102 and audible alarm 100 being activated until the interrupt relay 86 is manually reset or, instead, the "on" switch 82 is toggled off.

Once testing of the electrode 30 is complete, the electrosurgical test device provides 10 for easy cleaning by removing and replacing the used test sleeve assembly 14. The sleeve 14 is replaced by slidingly removing the electrode shaft 32 from the sleeve passageway 64 and disconnecting clip 48 from sleeve post 68. The sleeve 14 may then be disposed of and replace by a new sleeve. Replacement is conducted by simply attaching the clip 48 to the post 68 of the new sleeve 14.

Preferably, the test device 10 is used to inspected the electrode 30 in the sterile environment of an operating room just prior to performing a surgical procedure. Therefore, the risk of using an electrode with defective insulation during the surgical procedure is substantially reduced.

It will be appreciated by those skilled in the art that the power converter 74 can be omitted from the fault detection unit 12 if another suitable external high voltage source is available. In such an embodiment, the electrosurgical instrument is connected to the alternative voltage source. Then, the sleeve 14 and fault detector sensor 76 are used to check if current from the voltage source can be received through a defect in the electrosurgical instrument insulation. If the fault sensor 76 receives such an erroneous current, the detector 12 activates the audible and visual alarms 100, 102.

Figure 6:
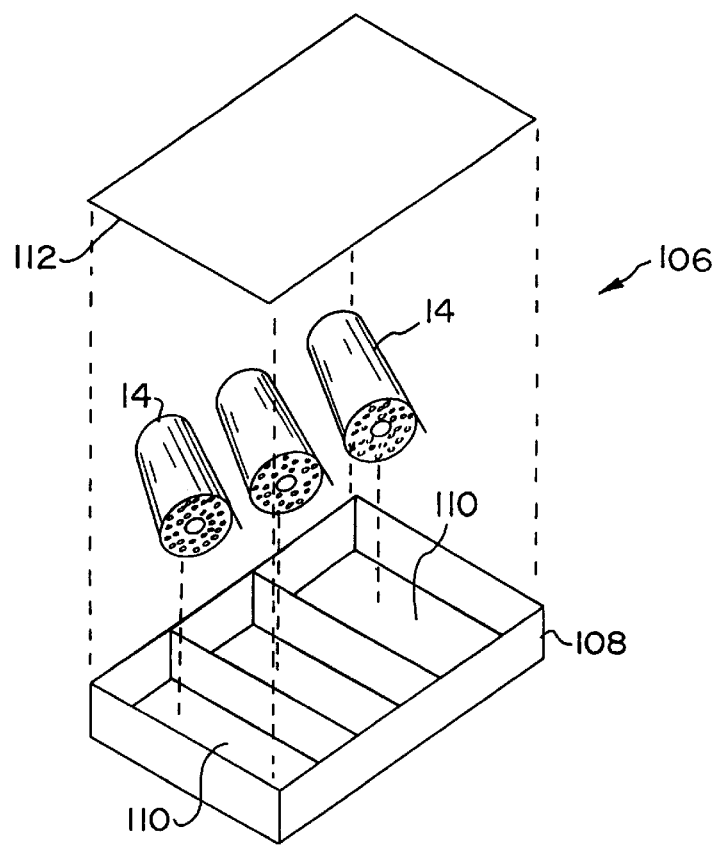
FIG. 6 is a perspective view of a plurality of test sleeve assemblies packaged within a protective receptacle.

As shown in FIG. 6, one or more test sleeve assemblies 14 may be sealed within an enclosure 106 for containment during shipping and storage. The enclosure 106 includes a bottom cover or tray 108, preferably formed from plastic in a vacuum-forming operation. The tray 108 may be provided with cavities or compartments 110 for individually receiving each sleeve 14 to be contained.

With one or more sleeves 14 placed in the tray 108, a cover member 112 is appropriately sealed to the tray 108. The top cover member 112 is preferably fabricated from spun-bonded plastic fibers, such as polyolefin fibers, e.g., TYVEK® fibers (DuPont Corporation). This material is preferred because it allows the package 106 to be sterilized after one or more sleeves 14 have been sealed within the enclosure.

Figure 7:
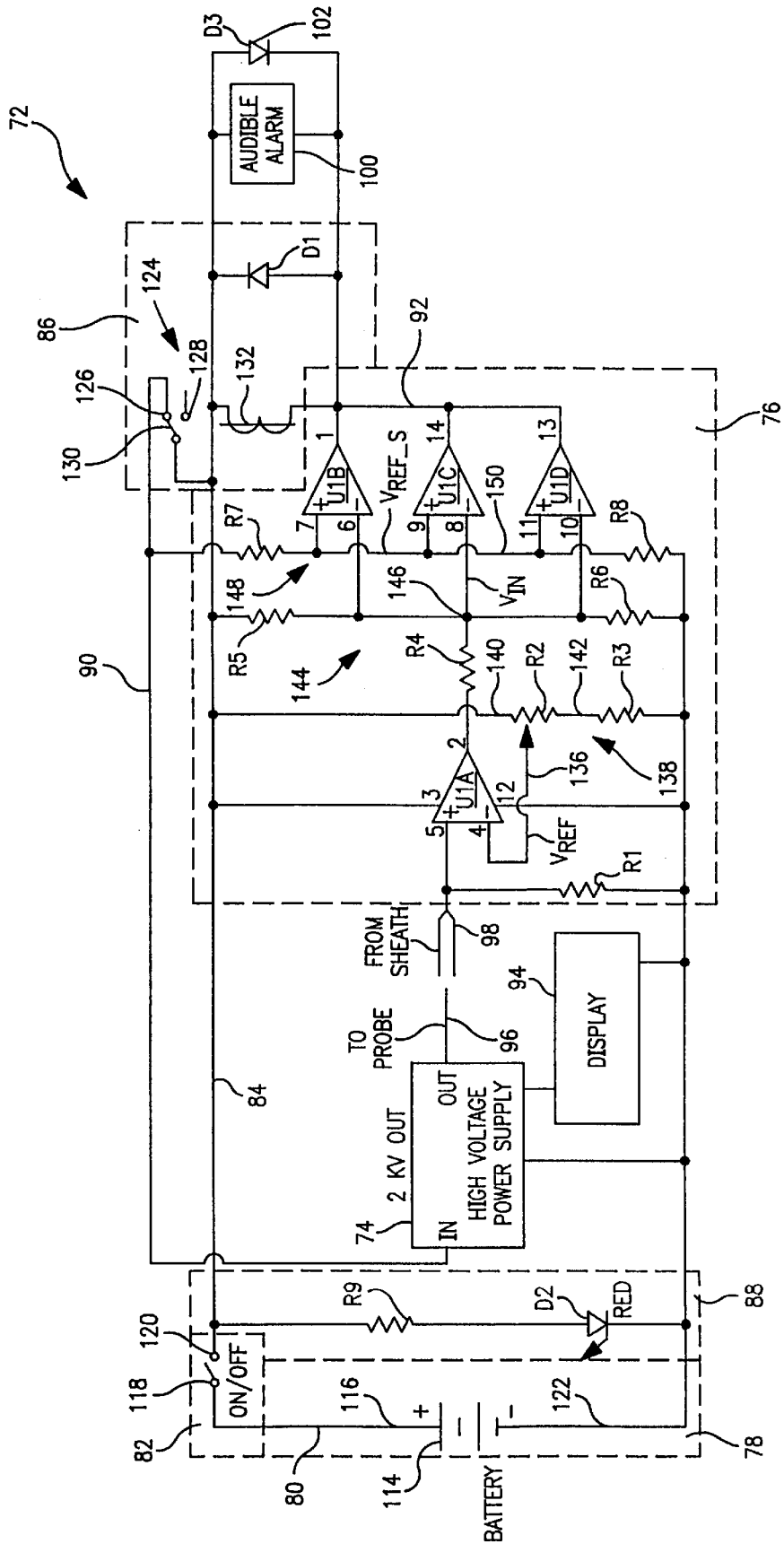
FIG. 7 is a detailed electrical schematic diagram of the fault detection unit illustrated in FIGS. 1 and 5.

Turning to FIG. 7, a detailed electrical schematic diagram of the detection circuitry illustrated in FIG. 5 is provided. It is to be understood that the embodiment shown in FIG. 7 is not intended to serve as a limitation upon the scope or teaching thereof, but is merely for the purpose of convenience of illustration of one embodiment of the detector circuit.

In FIG. 7, voltage source 78 consists of a battery 114 that is replaceably installed within the fault detection circuitry 72 in a conventional manner. Preferably, the battery 114 provides an unregulated DC voltage 80 of about nine volts (9V).

The positive terminal 116 of the battery is coupled to the "on" switch 82 for both enabling and removing power to and from, respectively, the fault detection circuitry 72. The "on" switch 82 consists of a conventional single-pole, single-throw (SPST) switch or the like. The "on" switch 82 has two terminals 118, 120 with terminal 118 connected to the voltage source 78 and terminal 120 operably connected, via lead 84, to the power indicator 88, interrupt relay 86, and sensor 76.

The power indicator 88 visually indicates if the "on" switch 82 has been selected to convey power to the fault detection circuitry 72. The power indicator 88 includes a current limiting resistor R9 and a Light Emitting Diode (LED) D2. Resistor R9 and LED D2 are connected in series to each other with the cathode of the LED D2 being coupled to the negative terminal 122 of the battery 114.

The interrupt relay circuitry 86 controls the enable signal 90 which: (1) provides power to the converter 74; and (2) latches the output of sensor 76. The interrupt relay circuitry 86 consists of a single-pole, double-throw (SPDT) latching relay 124 and a discharge protection diode D1. The relay 124 has a set of contacts 126, 128, an armature 130 and a coil 132.

One end of the relay coil 132 is coupled to both the anode of diode D1 and the fault detection signal 92 provided by the sensor 76. The other end of the relay coil 132 is connected to the cathode of diode D1 and the lead 84 extending from the "on" switch 82.

Lead 82 also is coupled to the relay armature 132. Further, relay contact 126 is coupled to the power converter 74. However, relay contact 128 is not connected.

The armature 130 of relay 124 is manually driven by an interconnected rod 134 (FIG. 1) to selectively form and maintain an electrical connection with contact 126. Thus, by connecting armature 130 to contact 126, lead 84 is coupled, via the enable signal 90, to the power converter 74 and the sensor 76.

Energizing the relay coil 132, as explained in detail below, results in the armature 130 breaking the electrical connection with contact 126 and coming into latching contact with relay contact 128. As a result, lead 84 is operably disconnected from enable signal 90.

Diode D1 provides protection for preventing inductive spikes from damaging relay coil 132 and possibly other components. The diode D1 forward conducts to furnish a route for the energy within the relay coil 132 to drain-off when power is removed from the coil after electrically switching the relay 124.

Sensor 76 includes four comparators U1A–U1D contained, preferably, within a single integrated circuit package which has a voltage input pin three (3) connected to terminal 120 of the "on" switch. Further, the voltage return pin twelve (12) of the integrated circuit package U1 is coupled to the negative terminal 122 of the battery 114.

Comparator U1A is configured to provide an input voltage comparator that is operated in an open-loop condition. As depicted in FIG. 7, the non-inverting input of comparator U1A is connected to a resistor R1 and the return terminal 20 of the fault detection unit 12. The opposite end of resistor R1 is connected to the negative terminal 122 of battery 114.

The inverting input of comparator U1A is coupled to the wiper 136 of a potentiometer R2 within an adjustable voltage divider 138 that includes resistor R3. The potentiometer R2 has two fixed resistance terminals 140, 142 with terminal 140 connected to lead 84. Further, potentiometer terminal 142 is coupled to resistor R3 which is tied to the negative terminal 122 of battery 114. Preferably, wiper 136 is selected to provide a reference voltage $V_{REF}$ of about 2.3 volts to the inverting input of comparator U1A.

Attached to the output of comparator U1A is an output voltage pull-up network 144 consisting of resistors R4, R5, and R6. The pull-up network 144 provides a voltage input $V_{IN}$ to the inverting inputs of comparators U1B–U1D for switching the fault detection output 92 of sensor 76.

Within the pull-up network 144, resistors R5 and R6 are connected in series between lead 84 and the negative terminal 122 of the battery 114. Further, the junction 146 between resistors R5 and R6 is coupled to the inverting input of comparators U1B–U1D and to one end of resistor R4. The other end of resistor R4 is tied to the output of comparator U1A.

Until a fault is detected, the comparator U1A pulls-down its output to substantially the same voltage potential as the negative terminal 122 of the battery 114 (i.e., zero volts). As such, the voltage input $V_{IN}$ provided to comparators U1B–U1D is pulled-down by comparator U1A to a preferred voltage potential of about 1.5 volts (1.5V).

However, if a fault is detected in the insulation of an electrode, then the output of comparator U1A is switched to an "open" state. Accordingly, the voltage input $V_{IN}$ received by the inverting inputs of comparators U1B–U1D is equal to the voltage at junction 146 which, preferably, is about six volts (6V).

Attached to the non-inverting inputs of comparators U1B–U1D is a switchable voltage divider 148 for providing a reference voltage $V_{REF\_S}$. The voltage divider 150 consists of resistors R7 and R8, connected in series, between enable signal 90 and the negative terminal 122 of battery 114.

Connected to the junction 150 between resistors R7 and R8 are the non-inverting inputs of the comparators U1B–U1D. Preferably, the junction 150 has a voltage potential of 4.5 volts (4.5) when the enable signal 90 is coupled to lead 84. Conversely, when the enable signal 90 is disconnected from lead 84, the junction voltage $V_{REF\_S}$ is substantially equal to the voltage potential at the negative terminal 122 of the battery 114 (i.e., zero volts).

The outputs of comparators U1B–U1D are tied together to jointly provide fault detect signal 92. Further, by tieing the outputs together, the comparators U1B–U1D provide sufficient current sinking capacity to simultaneously switch relay 86, active visual alarm 102, and activate audible alarm 100 which are attached between lead 96 and fault detect signal 92.

Before the fault detection circuitry 72 is employed in detecting flaws in electrosurgical instrument insulation, relay armature 130 is manually positioned by rod 134 (FIG. 1) to couple leads 84 and 90 together. Next, power is applied to the circuitry 72 by toggling switch 82 to an "on" position which connects voltage potential 80 to lead 84. As such, power is provided to relay 86, sensor 76, power converter 74, and indicator 88.

The application of power to the indicator 88, via lead 84, results in illumination of LED D2 which indicates that the fault detection circuitry 72 has been turned-on. Further, the power converter 74 provides a high voltage output of about 2 kilovolts which is received by the electrosurgical instrument to be tested.

Before a fault is detected in the insulation material of the electrosurgical instrument, the voltage potential at the non-inverting input of comparator U1A is generally equal to the voltage potential at the negative terminal 122 of battery 114 (i.e., zero volts). Correspondingly, with the non-inverting input at about zero volts and the inverting input at about 2.3 volts, the comparator U1A will pull its output to approximately the same voltage potential as the negative terminal 122 of the battery 114 (i.e., zero volts). This translates into a voltage of approximately 1.5 volts (1.5V) being received by the inverting inputs of comparators U1B–U1D.

The non-inverting inputs of comparators U1B–U1D receive a voltage potential of approximately 4.5 volts (4.5V), because, as stated above, leads 84 and 90 are tied together via relay 124. Thus, the outputs of comparators U1B–U1D are in an "open" state since the voltage potential at the non-inverting inputs (i.e., 4.5 volts) is greater than the voltage potential at the inverting inputs (i.e., 1.5 volts).

With the outputs of comparators U1B–U1D in an "open" state, the comparator outputs do not sink current. Accordingly, the failure of the comparators U1B–U1D to sink current via fault detection signal 92 results in the audible alarm 100 and visual alarm 102 being inactive. Thus, no fault is indicated by the fault detection circuitry 72.

Conversely, the presence of a fault in the electrosurgical instrument insulation results in the output 96 of the power converter 74 being essentially coupled to the non-inverting input of comparator U1A. Preferably, the power converter output 96 provides between 1–10 micro amps (1–10 μA) of current such that the non-inverting input of comparator U1A observes a voltage potential of about 2.5 volts (2.5V).

With the non-inverting input at about 2.5 volts and the inverting input at about 2.3 volts, the output of comparator U1A is switched to an "open" state. As such, the inverting inputs of comparators U1B–U1D received a voltage input $V_{IN}$ equal to about six volts (6V) which is greater than the switching voltage $V_{REF\_S}$ of 4.5V at the non-inverting inputs of the comparators.

Thus, detection of the fault results in the outputs of comparators U1B–U1D pulling the detection signal 92 to substantially the same voltage potential as the negative terminal 122 of the battery 114 (i.e., zero volts). As such, the comparators U1B–U1D provide a current sink for activating the audible alarm 100 and the visual alarm 102 to indicate the presence of a flaw in the insulation of the surgical instrument. Further, the sinking of current energizes relay coil 132 which results in relay armature 130 being disconnected from lead 90.

Severance of the connection between leads 90 and 84 causes power to be removed from the power converter 74 and the switchable voltage divider 148 within sensor 76. Accordingly, the output 96 of the power converter 74 is disabled and the non-inverting inputs of comparators U1B–U1D are effectively tied to the negative terminal 122 of the battery 114 (i.e., zero volts).

Dropping the reference voltage $V_{REF\_S}$ received by the non-inverting inputs of the comparators U1B–U1D to zero volts (0V) results in the inverting inputs being subjected to a greater voltage potential because, as stated above, the non-inverting input always receive a voltage potential of at least about 1.5 volts. Thus, the outputs of comparators U1B–U1D are latched to sink current regardless of whether the lining 52 within the test sleeve assembly 14 remains in contact with the conductive substrate of the electrosurgical instrument.

For completeness in the disclosure of the above-described fault detection circuitry, but not for purpose of limitation, the following representative values and component identifications are submitted. Those skilled in the art will recognized that many alternative elements and values may be employed in constructing the circuity in accordance with the present invention.

| Part | TYPE or VALUE |
| --- | --- |
| R1 | 1M Ohms |
| R2 | 10K Ohms |
| R3 | 1K Ohms |
| R4 | 1K Ohms |
| R5 | 4.7K Ohms |
| R6 | 10K Ohms |
| R7 | 4.7K Ohms |
| R8 | 4.7K Ohms |
| R9 | 1K Ohms |
| D1 | 1N4148 |
| U1 | LM3302 |

Figure 8:
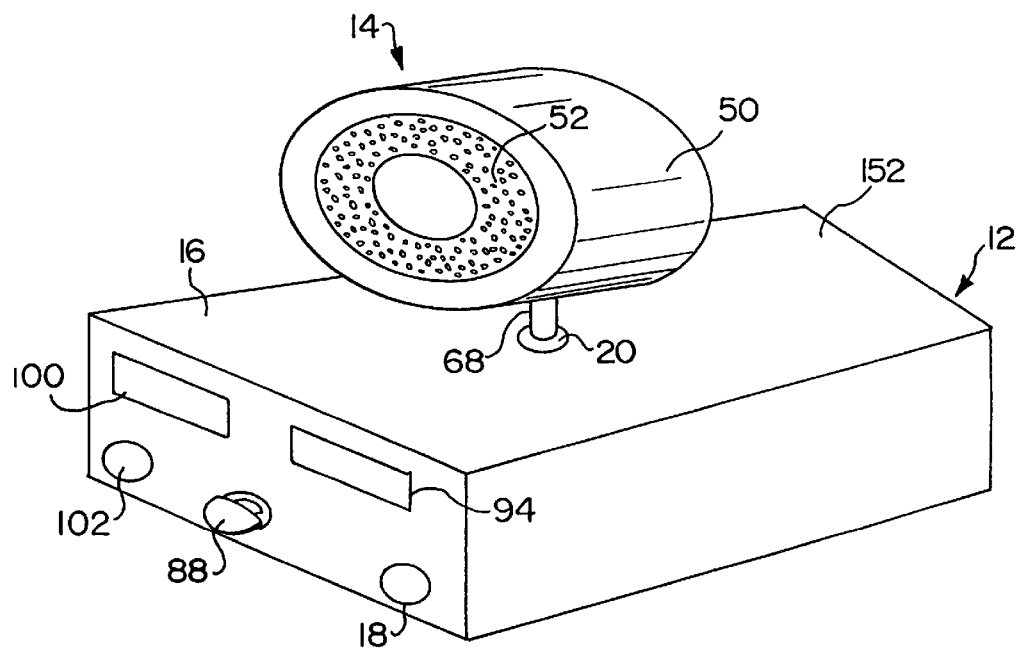
FIG. 8 is a top perspective view of another embodiment of an electrosurgical test device in accordance with the present invention wherein the test sleeve is removably rigidly secured to the fault detection unit.

FIG. 8 provides another embodiment of an electrosurgical test device. The embodiment of FIG. 8 is similar to that of FIG. 1 except that the test sleeve 14 is removably rigidly secured to the fault detection unit 12.

In FIG. 8, post 68 extends from the test sleeve assembly 14 and is received by the fault detection unit return terminal 20 in the top 152 of the housing 16. As such, a rigid conductive path from the sleeve 14 to the return terminal 20 of the fault detection unit 12 is provided by post 68.

Preferably, post 68 is generally perpendicular to the longitudinal axis of the test sleeve assembly sheath 50. The post 68 passes though the sheath 50 and into electrically conductive contact with lining 52. Further, the post 68 is secured to the sheath 50 by an adhesive or the like.

Connecting the post 68 directly to the return terminal 20 of the fault detection unit 12 eliminates the need for a return lead with a plug connector at one end and an alligator clip type connector on the other end. Instead, the test sleeve assembly 14 is plugged directly into the fault detection unit 12. In addition, because the post 68 is made of a stiff metal or metal alloy, the test sleeve assembly 14 is rigidly held to the fault detection unit 12.

It will be readily apparent from the foregoing detailed description of the invention and from the illustrations thereof that numerous variations and modifications may be effected without departing from the true spirit and scope of the novel concepts or principles of this invention.

I claim:

1. An apparatus for testing an electrosurgical instrument comprising:
   an electrically insulated rigid sheath defining an open bore;
   a resilient conductive lining attached to said sheath and defining an open passageway for receiving the electrosurgical instrument; and
   a fault detection circuit operably connected to said conductive lining for detecting a current path between said conductive lining and said electrosurgical instrument.

2. The apparatus of claim 1, wherein said fault detection circuit includes a sensor for generating a fault detection signal upon detection of said current path.

3. The apparatus of claim 2, wherein said fault detection circuit includes an interrupt relay responsive to said detection signal for commanding said sensor to latch said fault detection signal.

4. The apparatus of claim 3, wherein said fault detection circuit includes a switch operably connected to said sensor for connecting power to said sensor.

5. The apparatus of claim 4, wherein said fault detection circuit includes a power indicator operably connected to said switch for visually indicating said connecting of power to said sensor.

6. The apparatus of claim 2, wherein said fault detection circuit includes a visual alarm responsive to said fault detection signal for visually indicating detection of said current path.

7. The apparatus of claim 2, wherein said fault detection circuit includes an audible alarm responsive to said fault detection signal for audibly indicating detection of said current path.

8. The apparatus of claim 2, wherein said fault detection circuit includes a power converter for generating a high voltage output that is received by said electrosurgical instrument.

9. The apparatus of claim 1, wherein said lining consists of a conductive foam.

10. The apparatus of claim 9, wherein said conductive foam resiliently presses against said electrosurgical instrument.

11. The apparatus of claim 1, further including a post conductively coupled to said lining.

12. The apparatus of claim 11, wherein said post is generally in longitudinal axial alignment with said sheath.

13. The apparatus of claim 1, further including a tray for containing said sleeve.

14. An electrosurgical test device for testing a surgical instrument comprising:
   a disposable test sleeve assembly comprising:
      a sheath defining an open bore; and
      a resilient conductive lining attached to said sheath within said bore and defining an open passageway; and
   a fault detection circuit comprising:
      a sensor operably connected to said conductive lining for detecting a current path between said conductive lining and said surgical instrument, and said sensor generating a fault detection signal upon detection of said current path.

15. The electrosurgical test device of claim 14, wherein said fault detection circuit further includes an interrupt relay responsive to said detection signal for commanding said sensor to latch said fault detection signal.

16. The electrosurgical test device of claim 14, wherein said fault detection circuit further includes a switch operably connected to said sensor for connecting power to said sensor.

17. The electrosurgical test device of claim 16, wherein said fault detection circuit further includes a power indicator operably connected to said switch for visually indicating said connecting of power to said sensor.

18. The electrosurgical test device of claim 14, wherein said fault detection circuit further includes a visual alarm responsive to said fault detection signal for visually indicating detection of said current path.

19. The electrosurgical test device of claim 14, wherein said fault detection circuit further includes an audible alarm responsive to said fault detection signal for audibly indicating detection of said current path.

20. The electrosurgical test device of claim 14, wherein said fault detection circuit includes a power converter for generating a high voltage output that is received by said surgical instrument.

21. The electrosurgical test device of claim 14, wherein said conductive lining consists of a conductive foam that presses against said surgical instrument.

22. The electrosurgical test device of claim 14, wherein said test sleeve assembly further includes a post conductively coupled to said lining.

23. The electrosurgical test device of claim 22, wherein said post is generally in longitudinal axial alignment with said sheath.

24. The electrosurgical test device of claim 14, further including a package for containing said sleeve.

25. A method of testing insulation on an electrosurgical instrument comprising the steps of:
   (a) removing a test sleeve assembly from a tray, said test sleeve assembly having a sheath defining an open bore and a conductive lining mounted to said sheath and defining an open passageway;
   (b) sliding said electrosurgical instrument through said bore and said passageway;
   (c) pressing said conductive lining against said electrosurgical instrument as said electrosurgical instrument is slid though said bore and said passageway;

(d) detecting a current path between said lining and said electrosurgical instrument; and (e) generating a detection signal when said current path is detected.

26. The method of claim 25, further comprising the step of latching said fault detection signal.

27. The method of claim 25, further comprising the step of connecting a voltage source to a sensor for generating said detection signal.

28. The method of claim 27, further comprising the step of visually indicating whether said voltage source is connected to said sensor.

29. The method of claim 25, further comprising the step of visually indicating detection of said current path.

30. The method of claim 25, further comprising the step of audibly indicating detection of said current path.

31. The method of claim 25, further comprising the steps of generating a high voltage and conveying said high voltage to said electrosurgical instrument.

* * * * *